United States Patent
Binder et al.

(12)

(10) Patent No.: US 6,319,528 B1
(45) Date of Patent: *Nov. 20, 2001

(54) FEEDSTUFF ADDITIVE WHICH CONTAINS D-PANTOTHENIC ACID AND/OR ITS SALTS AND A PROCESS FOR THE PREPARATION THEREOF

(75) Inventors: Michael Binder, Steinhagen; Klaus-Erich Uffmann; Iiona Walger, both of Bielefeld; Ulrich Becker, Seice; Walter Pfefferle, Halle; Heinz Friedrich, Hanau, all of (DE)

(73) Assignee: Degussa Aktiengesellschaft, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/686,172

(22) Filed: Oct. 12, 2000

Related U.S. Application Data

(63) Continuation-in-part of application No. 09/431,097, filed on Nov. 1, 1999, now Pat. No. 6,238,714.

(30) Foreign Application Priority Data

May 5, 1999 (DE) .............................. 199 20 507
Mar. 31, 2000 (DE) .............................. 100 16 321

(51) Int. Cl.⁷ .................................................... A23L 1/302
(52) U.S. Cl. ............................ 426/72; 426/74; 426/656; 426/807
(58) Field of Search ................................... 426/656, 807, 426/74, 72

(56) References Cited

U.S. PATENT DOCUMENTS

| | | | |
|---|---|---|---|
| 2,918,370 | * 12/1959 | Helgren | ...................................... 99/2 |
| 3,862,337 | * 1/1975 | Osborne | ...................................... 426/2 |
| 4,552,775 | * 11/1985 | Baeling et al. | ...................... 426/624 |
| 5,133,976 | * 7/1992 | Rouy | ...................................... 426/2 |
| 5,431,933 | * 7/1995 | Binder et al. | ........................... 426/60 |
| 5,518,906 | * 5/1996 | Hikichi et al. | ........................ 435/116 |
| 5,622,710 | * 4/1997 | Binder et al. | ........................ 424/438 |
| 5,840,358 | * 11/1998 | Hofler et al. | .......................... 426/467 |

FOREIGN PATENT DOCUMENTS

| | | | |
|---|---|---|---|
| 598177 | * | 2/1948 | (GB) . |
| 784434 | * | 10/1957 | (GB) . |
| 96/33283 | * | 10/1996 | (WO) . |
| 97/36996 | * | 10/1997 | (WO) . |

* cited by examiner

Primary Examiner—Chhaya D. Sayala
(74) Attorney, Agent, or Firm—Pillsbury Winthrop LLP

(57) ABSTRACT

The invention provides a feedstuff additive based on a fermentation broth obtained by the fermentation of D-pantothenic acid producing microorganisms. The broth contains D-pantothenic acid, one or more salts of D-pantothenic acid, or mixtures thereof. Conversion of the broth to a solid, free-flowing form is achieved by drying or granulation

15 Claims, 3 Drawing Sheets

SEQUENCE LISTING

```
<160> NUMBER OF SEQ ID NOS: 2

<210> SEQ ID NO 1
<211> LENGTH: 62
<212> TYPE: DNA
<213> ORGANISM: Saccharomyces cerevisiae
<220> FEATURE:
<221> NAME/KEY: primer_bind
<222> LOCATION: (1)..(62)
<223> OTHER INFORMATION: START END OF THE READING FRAME YHR063c

<400> SEQUENCE: 1
gcgcgaattc agatccgcgg ccgcaaagag gagaaattaa ctatgactgc accacacaga      60
ag                                                                    62

<210> SEQ ID NO 2
<211> LENGTH: 36
<212> TYPE: DNA
<213> ORGANISM: Saccharomyces cerevisiae
<220> FEATURE:
<221> NAME/KEY: primer_bind
<222> LOCATION: (1)..(36)
<223> OTHER INFORMATION: STOP END OF THE READING FRAME YHR063c

<400> SEQUENCE: 2
cgcgactagt ctgcagtcag tcctttctcc agtcac                               36
```

FEEDSTUFF ADDITIVE WHICH CONTAINS D-PANTOTHENIC ACID AND/OR ITS SALTS AND A PROCESS FOR THE PREPARATION THEREOF

This is a Continuation-in-Part of National Appln. No. 09/431,097 filed Nov. 1, 1999, now U.S. Pat. No. 6,238,714.

CROSS-REFERENCE TO RELATED APPLICATION

This application is based on German Application Nos. DE 199 20 507.8, filed May 5, 1999 and DE 100 16 321.1, filed Mar. 31, 2000, which disclosures are incorporated herein by reference.

FIELD OF THE INVENTION

The invention relates to an animal feedstuff additive based on a fermentation broth, which contains D-pantothenic acid and/or one or more of its salts and a process for preparing this additive.

BACKGROUND OF THE INVENTION

Pantothenic acid is produced all over the world on a scale of several thousand tonnes per year. A large part of the pantothenic acid produced is used for feeding economically useful animals such as poultry and pigs. Demand is increasing.

Pantothenic acid may be prepared by chemical synthesis or biotechnically by the fermentation of suitable microorganisms in suitable nutrient solutions. In the case of chemical synthesis, DL-pantolactone is an important precursor. It is prepared in a multi-stage process from formaldehyde, isobutylaldehyde and cyanide. In further process steps, the racemic mixture is separated and D-pantolactone is condensed with β-alanine, thus producing D-pantothenic acid.

The typical commercial form is the calcium salt of D-pantothenic acid. The calcium salt of the racemic mixture of D,L-pantothenic acid can also be used.

The advantage of fermentative preparation using microorganisms is the direct formation of the desired stereoisomeric form, that is the D-form, which contains no L-pantothenic acid.

Various types of bacteria such as, for example, *Escherichia coli, Arthrobacter urea faciens, Corynebacterium erythrogenes, Brevibacterium ammoniagenes* and also yeasts such as, for example, *Debaromyces castellii* may, as shown in EP-A-0 493 060, EP-A-0 590 857 and WO 97/10340, produce D-pantothenic acid under suitable conditions of fermentation. Particularly suitable microorganisms are the derivatives of *Escherichia coli* IFO3547 described therein, such as e.g. the strains FV5069/pFV31 or FV5069/pFV202.

During the fermentative preparation of D-pantothenic acid, as described in EP-A-0 493 060, EP-A-0 590 857 and WO 97/10340, a microorganism capable of D-pantothenic acid production is cultivated in a suitable nutrient and the D-pantothenic acid produced is then isolated in a costly manner, purified and prepared as the calcium salt.

Suitable nutrient media contain a source of carbon such as e.g. glucose or starch flour hydrolyzate or sucrose or molasses, precursors such as e.g. β-alanine,D,L-pantoic acid or D,L-pantolactone, a source of nitrogen such as e.g. ammonium sulfate, a source of phosphorus such as e.g. potassium phosphate and other salts, trace elements and vitamins and optionally complex media additives such as e.g. yeast extract. The microorganisms are then incubated in this medium at a suitable pH, with appropriate aeration and stirring, wherein these then excrete D-pantothenic acid.

According to the current prior art, which is represented by WO96/33283 and EP-A-0 590857, the calcium salt of D-pantothenic acid is obtained from the pantothenic acid-containing fermentation broth by costly isolation and purification. After initial isolation of the biomass by filtering or centrifuging, further processing of the filtrate is performed by purification using active carbon or column chromatography. After reaction of the solutions obtained in this way with calcium hydroxide, the desired Ca salt crystallizes out.

According to WO 96/33283 the filtrate is decolored with active carbon in the first column. The pH is adjusted to 3.0 with concentrated hydrochloric acid and the liquid is then continuously purified over two further columns packed with active carbon. Elution of the D-pantothenic acid is achieved with the aid of methyl alcohol. After the subsequent neutralization step using $Ca(OH)_2$ powder, a solution is obtained from which calcium D-pantothenate is recovered by crystallization at 5° C.

In the method described in EP-A-0 590 857, the filtrate is first purified with the aid of cation and anion exchanger columns. Elution is performed with hydrochloric acid. The eluted fraction is then neutralized with $Ca(OH)_2$, active carbon is added thereto and the mixture is filtered. The filtrate obtained is then extracted into a low molecular weight alcohol (methanol, ethanol, isopropanol) and calcium D-pantothenate is obtained by crystallization.

The calcium D-pantothenate prepared in the way described above is used as an additive in feedstuff for animal nutrition.

SUMMARY OF THE INVENTION

According to the prior art, salts of D-pantothenic acid and D,L-pantothenic acid are prepared by reacting the acid, prepared by chemical synthesis or fermentation, with the desired salt solutions.

The object of the invention is to provide new preparative forms of D-pantothenic acid and its salts which are suitable as feedstuff additives.

Furthermore, an object of the invention is to provide a method of preparation which is more economical and more efficient than the currently known processes.

The invention provides an animal feedstuff additive based on a fermentation broth, characterized in that it contains p1 a) D-pantothenic acid and/or its salts, in particular alkali metal or alkaline earth metal salts, p1 b) the biomass formed during fermentation in an amount of 0 to 100% and p1 c) at least the greater part of the other dissolved ingredients of the fermentation broth and p1 d) is present in solid form, in particular in a finely divided or granulated and free-flowing form.

Depending on the requirements, the animal feedstuff additives are generally provided as spray dried or freeze-dried, finely divided, free-flowing powders, or else in granulated form, which may contain different proportions of biomass. The bulk density is in particular about 500 kg/m³. The additives are storage-stable.

If the biomass is isolated, naturally other solids, for example inorganic solids, are also removed. In addition, the additive according to the invention contains at least the greater part of the other substances produced or any added substances which are present dissolved in the fermentation broth, provided they have not been separated by suitable processes.

These substances may include organic secondary products which are produced and excreted by the microorganisms used during fermentation, in addition to D-pantothenic acid. These include L-amino acids chosen from the group L-methionine, L-lysine, L-valine, L-threonine, L-alanine or L-tryptophane, in particular L-valine. Furthermore, organic acids which contain up to three carboxyl groups such as e.g. acetic acid, lactic acid, citric acid, malic acid or fumaric acid are also included. Finally, sugars which are poorly convertible, such as e.g. trehalose, are also included. These compounds are optionally desirable if they contribute to the value of the additive.

Furthermore these substances may include groupings from the convertible sugars used such as e.g. glucose or saccharose.

The invention also provides a process for preparing a feedstuff additive which contains D-pantothenic acid and/or its salts, which is characterized in that p1 a) the D-pantothenic acid-containing broth which generally contains sodium, potassium, ammonium, magnesium or calcium salts is prepared by fermentation, p1 b) the biomass is optionally completely or partly separated from this, p1 c) the hydroxide or oxide of an alkaline earth or alkali metal is added to the solution or broth obtained in this way, preferably in stoichiometric amounts with respect to the D-pantothenic acid, and p1 d) the mixture obtained in this way is dried, spray dried, spray granulated or granulated.

The invention also provides a process for preparing feedstuff additives which contain D-pantothenic acid and/or its sodium, potassium, ammonium, magnesium or calcium salts in the range from 20 to 80 wt. % (dry weight) from fermentation broths, characterized by the steps p1 a) preferably, removal of water from the fermentation broth (concentration step), p1 b) optionally, removal of 0 to 100% of the biomass formed during fermentation, p1 c) addition of one or more of the compounds mentioned to the fermentation broths obtained in accordance with a) and b), wherein the weight of compounds added is such that their total concentration in the animal feedstuff additive is in the range from about 20 to 80 wt. %, in particular 50 to 80 wt. %, p1 d) drying the fermentation broths obtained in accordance with c) in order to obtain the animal feedstuff additive in the desired powdered or granulated form.

Fermentation broths which have been obtained using microorganisms suitable for the production of D-pantothenic acid and which contain D-pantothenic acid and/or its salts are suitable for the process according to the invention.

The microorganisms may be fungi or yeasts such as for example *Debaromyces castellii* or Gram-positive bacteria for example from the genus Corynebacterium or Gram-negative bacteria such as for example those from the Enterobacteriaceae family. The genus Escherichia which includes the species *Escherichia coli* is mentioned in particular from the family of Enterobacteriaceae. Within the species *Escherichia coli*, the so-called K-12 strains such as for example the strains MG1655 or W3110 (Neidhard et al.: *Escherichia coli* and Salmonella. Cellular and Molecular Biology (ASM Press, Washington D.C.) or *Escherichia coli* wild type strain IFO3547 (Institut fur Fermentation, Osaka, Japan) and mutants derived therefrom may be mentioned. Again, among the strains prepared from IFO3547, those named FV5069/pFV31 (EP-A-0 590 857) and FV5069/pFV202 (WO 97/10340) are exceptional. The species *Corynebacterium glutamicum* is mentioned in particular from the genus Corynebacterium.

The microorganisms mentioned above may be cultivated continuously or batchwise in a batch process or a fed-batch process or a repeated fed-batch process for the purpose of D-pantothenic acid production. Summaries of known methods of cultivation are given in the textbook by Chmiel (Bioprozesstechnik 1. Einführung in die Bioverfahrenstechnik (Gustav Fischer Verlag, Stuttgart, 1991) or in the textbook by Storhas (Bioreaktoren und periphere Einrichtungen (Vieweg Verlag, Braunschweig/ Wiesbaden, 1994).

The culture medium being used must satisfy the requirements of the particular microorganisms in an appropriate manner. Descriptions of culture media for various microorganisms are given in "Manual of Methods for General Bacteriology" produced by the American Society for Bacteriology (Washington D.C., USA, 1981). Sugars and carbohydrates such as e.g. glucose, saccharose, lactose, fructose, maltose, molasses, starch and cellulose, oils and fats such as e.g. soya oil, sunflower oil, peanut oil and coconut fat, fatty acids such as e.g. palmitic acid, stearic acid and linoleic acid, alcohols such as e.g. glycerol and ethanol and organic acids such as e.g. acetic acid may be used as sources of carbon. These substances may be used separately or as a mixture. Organic nitrogen-containing compounds such as peptones, yeast extract, meat extract, malt extract, maize steep liquor, soybean meal and urea or inorganic compounds such as ammonium sulfate, ammonium chloride, ammonium phosphate, ammonium carbonate and ammonium nitrate may be used as sources of nitrogen. The sources of nitrogen may be used separately or as a mixture. Potassium dihydrogen phosphate or dipotassium hydrogen phosphate or the corresponding sodium-containing salts may be used as sources of phosphorus. The culture medium must also contain salts of metals, such as e.g. magnesium sulfate or iron sulfate, which are required for growth. Finally, essential growth-promoting substances such as amino acids and vitamins are also used in addition to the substances mentioned above. In addition, precursors of D-pantothenic acid such as aspartate, $\beta$-alanine, ketoisovalerate, ketopantoic acid or pantoic acid and optionally their salts may also be added to the culture medium. The feedstocks mentioned may be added to the culture in the form of a one-off batch or may be fed to the culture in a suitable manner during cultivation.

Ammonia or ammonia water are preferably used to regulate the pH. Other basic compounds such as sodium hydroxide or potassium hydroxide are optionally suitable. If acid compounds are required, phosphoric acid or sulfuric acid are used in an appropriate manner. To control the production of foam, anti-foam agents, such as e.g. fatty acid polyglycol esters, are used. Suitable selectively acting substances e.g. antibiotics are optionally added to the medium to maintain the stability of plasmids. In order to maintain aerobic conditions, oxygen or oxygen-containing gas mixtures such as e.g. air are passed into the culture. The temperature of the culture is normally 20° C. to 45° C. and preferably 25° C. to 40° C. The culture procedure is continued until a maximum of D-pantothenic acid has been produced. This target is generally reached within 10 hours to 160 hours.

The fermentation broths obtained in this way generally have a dry weight of 7.5 to 25 wt. % and contain D-pantothenic acid at a concentration of >0 to 20 wt. %. Fermentation processes in which the D-pantothenic acid amounts to 2 to 20 wt. % of the dry weight after completion of fermentation are particularly advantageous. It is also advantageous if the fermentation process is performed in a sugar-limited manner, at least at the end, but advantageously over at least 30% of the fermentation time. That is, the concentration of convertible sugars in the fermentation medium is held at ≧0 to 3 g/l or is lowered thereto during this time.

In a variant containing ammonium ions for preparing the additive according to the invention, the biomass is optionally initially removed completely or partly from the D-pantothenic acid-containing fermentation broths, by known separation methods such as for example centrifuging, filtering, decanting or a combination thereof. According to the invention, however, it is also possible to leave the entire biomass in the fermentation broths. Finally, 0.8 to 1.2, preferably 0.95 to 1.1 equivalents of an oxide or hydroxide of an alkali metal or alkaline earth metal, in particular NaOH, KOH, Ca(OH)$_2$ or MgO, with respect to the D-pantothenic acid, is generally added to this broth. In the case of low D-pantothenic acid concentrations, it may also be advantageous to use much larger amounts of the oxides or hydroxides, for example in the range 1.2 to 4 equivalents. The suspension obtained in this way is generally concentrated to a maximum of 60 wt. % dry weight before drying. It is also possible to concentrate the fermentation broth first and then add the oxides or hydroxides. The concentrate obtained is then converted to a pourable, free-flowing, finely divided powder or to granules in a conventional dryer or, for example using a falling film evaporator or a thin film evaporator or a spray dryer or a spray granulator or a freeze-drying unit. Granulation may also take place after drying, for example in the form of build-up granulation.

Furthermore, the inventors have found a new method of preparing ammonium, potassium, sodium, magnesium or calcium D-pantothenic acid-containing powders or forms of presentation which contain these in a rapid and cost-effective manner. For this, a D-pantothenic acid-containing fermentation broth is prepared using the corresponding hydroxyl compound, the biomass is optionally first removed, completely or partly, by known separation methods such as for example centrifuging, filtering, decanting or a combination thereof. According to the invention, however, it is also possible to leave the entire biomass in the fermentation broth. Then the optionally pre-treated broth is concentrated or dried out using known methods such as for example by using a rotary evaporator or a thin film evaporator or a falling film evaporator. The optionally pre-treated broth is then processed to give a pourable, free-flowing, finely divided powder, or granules, using the methods of spray-drying, spray granulation or freeze-drying or some other process.

The new animal feedstuff additives according to the invention generally contain 20–80 wt. %, preferably 30–75 wt. % of D-pantothenic acid and/or its salts, with respect to the total weight. They generally also contain inorganic constituents in an amount of 2.5–25 wt. % and optionally organic secondary products in an amount of >0 to 30 wt. %. The proportion of dry biomass amounts to 0 to 35 wt. %. The water content is preferably ≦5 wt. %. The desired concentration of D-pantothenic acid and/or one or more of the salts mentioned is optionally produced by adding the corresponding compounds to the fermentatively produced products. The desired compounds are preferably added to the mixture in the form of solutions or dry substances and mixed with this before drying or spray drying, in particular after concentrating the mixture. The product obtained in this way is used as a feedstuff additive.

The concentration of D-pantothenic acid may be determined using known methods (Velisek; Chromatographic Science 60, 515–560 (1992).

BRIEF DESCRIPTION OF THE DRAWINGS

The invention is further described in the Figures in which.

Figure 1:
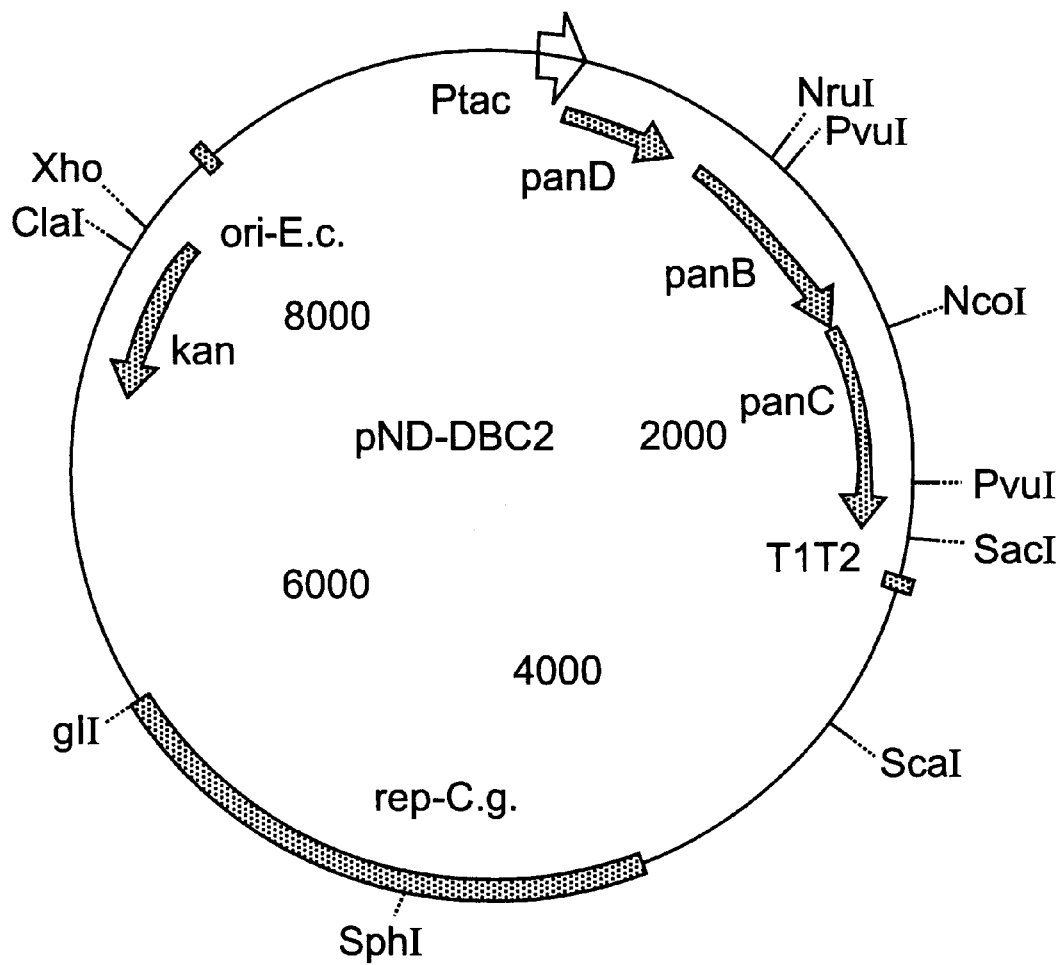
FIG. 1 shows a chart of plasmid pND-DBC2.

A key to the abbreviations used is given below:

Regarding FIG. 1:

rrnBT1T2: transcriptions-terminator of the rrnB gene

Ptac: tac promoter panB: encoding region of the panB gene panC: encoding region of the panc gene panD: encoding region of the panD gene rep-C.g.: DNA region for replication in *C. glutamicum* oriV-E.c.: origin of vegetative transfer in *E. coli* kan: resistance gene for kanamycin

BglII: cleavage site of restriction enzyme BglII

ClaI: cleavage site of restriction enzyme ClaI

NcoI: cleavage site of restriction enzyme NcoI

NruI: cleavage site of restriction enzyme NruI

PvuI: cleavage site of restriction enzyme PvuI

SacI: cleavage site of restriction enzyme SacI

SalI: cleavage site of restriction enzyme SalI

ScaI: cleavage site of restriction enzyme ScaI

SphI: cleavage site of restriction enzyme SphI

XhoI: cleavage site of restriction enzyme XhoI.

Figure 2:
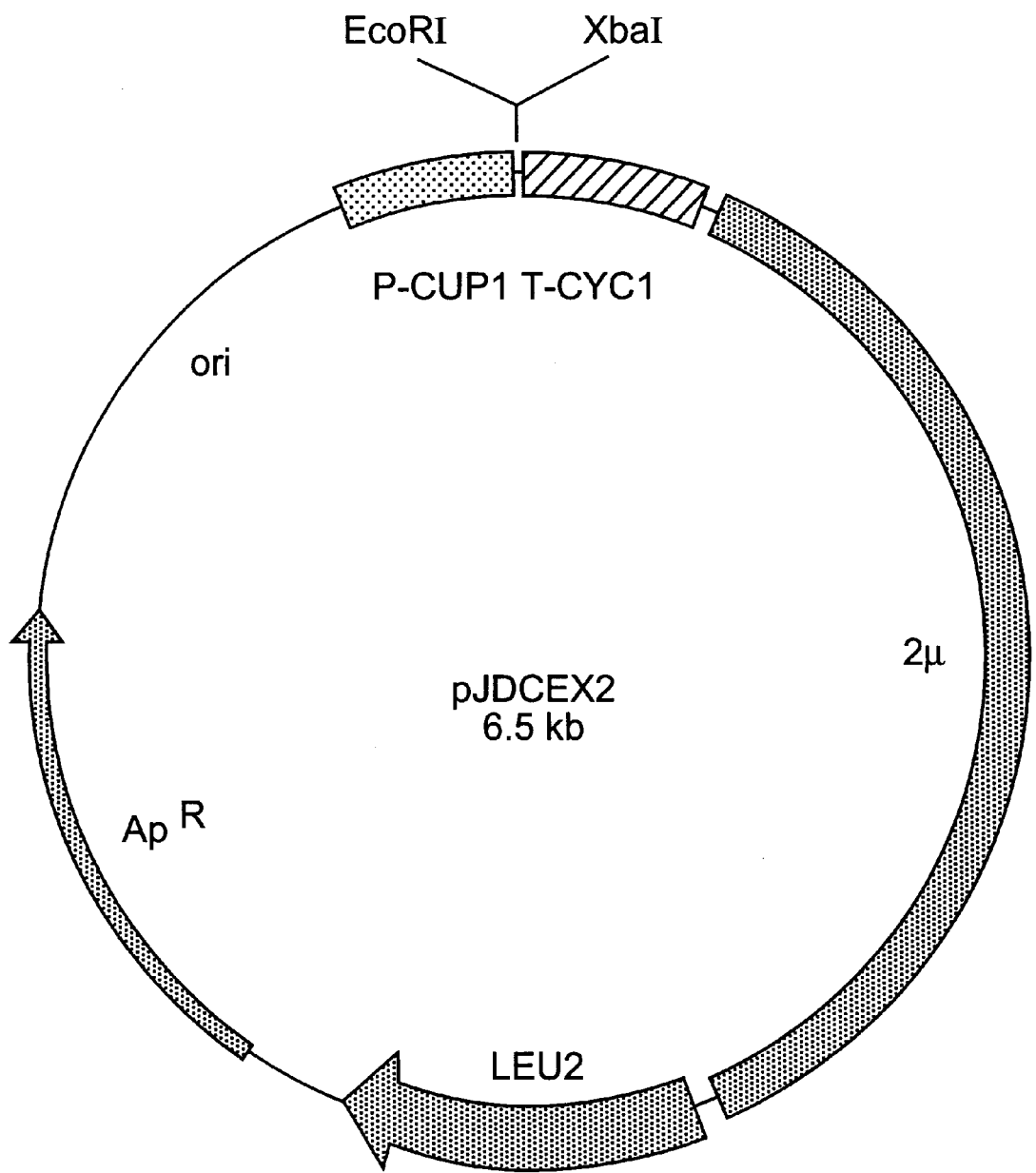
FIG. 2 shows a chart of plasmid pJDCEX2.
Figure 3:
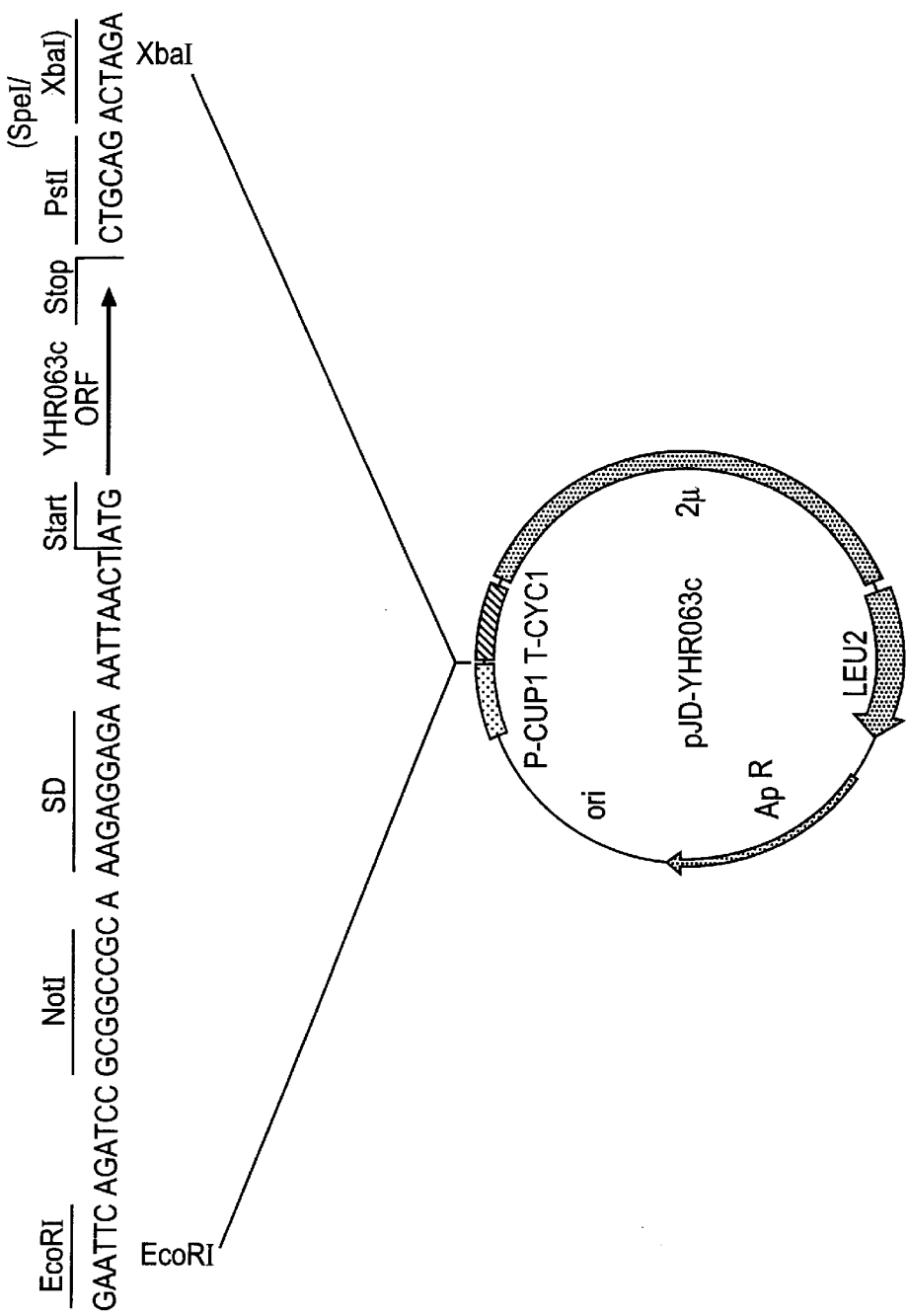
FIG. 3 shows a chart of plasmid pJD-YHR063c.

Regarding FIGS. 2 and 3:

LEU2: beta-isopropylmalate dehydrogenase gene of *Saccharomyces cerevisiae*

2µ: sequences of endogenous 2µ plasmid of *Saccharomyces cerevisiae*

Ap$^R$ beta-lactamase gene

P-CUP 1: promoter of *Saccharomyces cerevisiae* CUPI gene (metallothioneine)

T-CYC1: terminator of CYC1 gene (cytochrome C) of *Saccharomyces cerevisiae*

SD: Shine Dalgarno sequence

EcoRI: cleavage site of restriction enzyme EcoRI

NotI: cleavage site of restriction enzyme NotI

SpeI: cleavage site of restriction enzyme SpeI

XbaI: cleavage site of restriction enzyme XbaI

DETAILED DESCRIPTION OF THE INVENTION

EXAMPLES

The present invention is explained in more detail in the following working examples. For this purpose, trials were performed with the D-pantothenic acid producing strain *Escherichia coli* 5069/pFV31, which is deposited as FERM-BP 4395, in accordance with the Budapest convention, at the Fermentation Research Institute, Agency of Industrial Science and Technology in 1-1-3, Higashi, Tsukuba-shi, Ibaraki (Japan).

Example 1

Preparing a D-Pantothenic Acid-containing Fermentation Broth

1. Preparing the Inoculum

A sample of *Escherichia coli* FV5069/pFV31 was painted onto LBG agar which had been supplemented with 50 µg per ml of ampicillin. This agar plate culture was incubated for 17 hours at 37° C. and then stored in a refrigerator at +4° C. Selected individual colonies were then propagated further in LBG broth. LBG broth has the following composition: 10 g/l peptone, 5 g/l yeast extract, 5 g/l Nacl and 1 g/l glucose. LBG agar also contains 12 g/l agar. Ready prepared preparations can be purchased from Gibco/BRL (Paisley, Scotland, Great Britain) as LB broth base or LB agar. After adding 1 g/l glucose, the medium mentioned above is then obtained. Cultures of 10 ml, which were placed in 100 ml conical flasks, were incubated for 16 hours at 37° C. and 180 rpm in an ESR incubator from Kühner AG (Birsfelden, Switzerland). Then the cell suspension was centrifuged out in a J-6B centrifuge from Beckmann (Hannover, Germany) for 15 minutes at 4000 rpm. The cell pellet was resuspended in 10 ml of LBG medium which had been supplemented with 20% of glycerol and bottled in 10 aliquots of 1 ml each, under sterile conditions and frozen at −70° C. These cultures were used as a master cell bank.

To prepare a working cell bank, LBG medium which had been supplemented with 50 μg/ml of ampicillin, was shared between 100 ml conical flasks in 10 ml portions and then inoculated with 100 μl of the master cell bank described above. The mixtures were incubated for 16 hours at 37° C. and 180 rpm in an ESR incubator from Kühner AG (Birsfelden, Switzerland). After incubation, the optical density (OD) of the culture suspension was determined using a LP2W photometer from the Dr. Lange Co. (Berlin, Germany) at a measurement wavelength of 660 nm. It was 3.5. Then the cell suspension was placed in sterile 30 ml polyethylene tubes from the Greiner Co, (Frickenhausen, Germany) under sterile conditions, and centrifuged out at 2500 rpm for 15 minutes using a J-6B centrifuge from Beckmann (Hannover, Germany). The separated biomass was resuspended in 10 ml of LBG medium which had been supplemented with 20% of glycerol. Then the cell suspension was placed, in 500 μl portions, in 1 ml sterile tubes from the Nalgene Co. (New York, U.S.A.) under sterile conditions and frozen at −70° C. The preserved portions prepared in this way were used as a working cell bank.

2. Preparing a D-Pantothenic Acid-containing Fermentation Broth

To prepare a pantothenic acid-containing fermentation broth, the working cell bank was first multiplied in a shaking flask culture and this was used to inoculate a pre-fermenter. The culture from the pre-fermenter was used to inoculate the production fermenter.

SKA medium was used for the shaking flask culture. SKA medium was prepared as described in the following. 7.0 g $(NH_4)_2SO_4$, 0.5 g $KH_2PO_4$, 1.0 g $K_2HPO_4$, 0.5 g $MgSO_4*7H_2O$, 0.01 g $MnSO_4*H_2O$, 0.01 g $ZnSO_4*7H_2O$, 0.005 g $Fe_2(SO_4)_3$, and 20 g of maize steep liquor, which had previously been adjusted to a pH of 6.8 with 25% strength ammonia solution, were weighed into a 1 l glass beaker and then 875 ml of distilled water were added thereto. This maize steep liquor-containing salt solution was sterilized in an autoclave at 121° C. for 20 minutes. Furthermore, a solution consisting of 125 g of distilled water, 28.7 g glucose and 0.002 g thiamine*HCl was sterilized by filtration. 10 g of $CaCO_3$ were weighed into a 100 ml flask and sterilized in an autoclave at 123° C. for 20 minutes. SKA medium was obtained by combining the two components mentioned above with the maize steep liquor-containing salt solution.

This SKA medium was divided into 12.5 ml portions in 100 ml conical flasks and then inoculated with 0.5 ml of a cell suspension. A preserved portion of the working cell culture, diluted 1:100 with sterile physiological saline was used as the cell suspension. Incubation was performed for 20 hours at 32° C. and 150 rpm in a RC-1-TK incubator from Infors AG (Bottmingen, Switzerland). The optical density at a measurement wavelength of 660 nm (OD 660) determined after this procedure was 12.5.

0.5 ml of this shaking flask culture were diluted with 4.5 ml of physiological saline and of that 0.7 ml were used to inoculate 1300 ml of culture medium which had been initially placed in a 2 l laboratory fermenter model Biostat® MD from Braun Diessel Biotech GmbH (Melsungen, Germany).

The culture medium was prepared as follows. A solution consisting of 9.81 g $(NH_4)_2SO_4$, 0.7 g $KH_2PO_4$, 1.402 g $K_2HPO_4$, 0.70 g $MgSO_4*7H_2O$, 0.0014 g $MnSO_4*H_2O$, 0.014g $Fe_2(SO_4)_3$ and 28.04 g maize steep liquor in 1300 ml of tap water was adjusted to a pH of 6.5 with 25% strength ammonia solution and sterilized in an autoclave at 121° C. for 20 minutes. To this maize steep liquor-containing salt solution was added a separate sterile-filtered solution which contained 40.62 g glucose and 0.0042 g thiamine*HCl in 100 g of distilled water, under sterile conditions.

Fermentation was performed for 16 hours at 37° C. and with a rate of aeration of 1 vvm. The dissolved oxygen was kept at 20% and the pH was kept at 6.5. 25% strength ammonia solution was used as the pH regulating agent. The optical density was 13.1.90 ml of this culture was used to inoculate 1144 ml of growth medium for the main fermentation procedure in a 2 l laboratory fermenter, Biostat® MD model.

The growth medium was prepared as follows. A solution consisting of 4.14 g $(NH_4)_2SO_4$, 0.744 g $KH_2PO_4$, 1.0 g $K_2HPO_4$, 0.83 g $MgSO_4*7H_2O$, 0.0124 g $MnSO_4*H_2O$, 18.87 g β-alanine, 0.74 g Struktol J647 and 49.72 g of maize steep liquor in 1144 ml of tap water was adjusted to a pH of 6.5 with 25% strength ammonia solution and sterilized in an autoclave at 121° C. for 20 minutes. To this maize steep liquor-containing salt solution was added a separate sterile-filtered solution which contained 35.92 g glucose and 0.002 g thiamine*HCl in 100 ml of distilled water, under sterile conditions.

Fermentation was performed for 40 hours at 37° C. In the growth phase the pH was 6.5 and the rate of aeration was 1 vvm. In the production phase the pH was 6.0 and the rate of aeration was 1.5 vvm. The dissolved oxygen was maintained at less than 2% in both phases. The 25% strength ammonia solution was used as the pH regulating agent. During fermentation, production medium 1 and production medium 2 were fed step-wise. Maize steep liquor was added in one portion during cultivation. The production medium contained 465.29 g glucose and 0.0261 g thiamine*HCl in 584 ml of tap water and had been sterile-filtered. Production medium 2 contained 37.5 g β-alanine in 140 ml of tap water which had been sterilized in an autoclave at 121° C. for 20 minutes. After a fermentation time of 7.5 hours and up to the end of the cultivation stage, production medium 1 was fed stepwise. After 10.5 hours of cultivation, 49.5 g of maize steep liquor which had been dissolved in 100 ml of tap water and sterilized for 20 minutes at 121° C. in an autoclave, were added, under sterile conditions. After a fermentation time of 12.5 hours and up to the end of the cultivation stage, production medium 2 was fed at a rate of addition of 3.5 g/h. After 41 hours of cultivation, a pantothenic acid concentration of 6.1 wt. % was found in the fermentation broth.

The concentration of D-pantothenic acid was determined using a HPLC (high performance liquid chromatography) unit model M321 from Knauer (Berlin, Germany) by means of RI (refractive index) detection using a Hypersil APS2 amino phase with 5 μm particle size.

Example 2

In a fermentation trial which was performed under the same conditions as described in Example 1, a pantothenic acid concentration of 5.4 wt. % was detected in the fermentation broth after a cultivation time of 43 hours. The concentration of L-valine was 8 g/l.

Example 3

Preparing Calcium D-Pantothenate

The biomass was first separated from a pantothenic acid-containing fermentation broth which had been prepared using the process described in Examples 1 and 2 and which contained about 6.1 wt. % of D-pantothenic acid. For this, 1 l of the fermentation broth mentioned above was centrifuged using a laboratory centrifuge, a Biofuge-Stratos model from Heraeus (Düsseldorf, Germany), for 20 minutes at 4,000 rpm and the supernatant centrifuge liquid was purified further by cross-flow ultrafiltration using an MRC polymer membrane of 30kD in an UF unit from ICT GmbH (Bad Homburg, Germany).

Then 10.1 g of solid $Ca(OH)_2$ (96%; Merck, Darmstadt, Germany) were added batchwise, with stirring. The pH was then about 10.3. The broth treated in this way was then concentrated under vacuum at 60° C. in a rotary evaporator, a Rotavapor RE-120 from Büchi-Labortechnik GmbH (Konstanz, Germany) to a liquid content of about 50% dry weight. The concentrated broth obtained in this way was then spray dried to prepare the calcium salt of D-pantothenic acid. For this, a laboratory spray dryer, a Büchi-190 from Büchi-Labortechnik GmbH (Konstanz, Germany), was used with an inlet temperature of 107° C., an outlet temperature or 85° C., a pressure difference of −40 mbar and a rate of flow of air of 600 NL/h.

The calcium D-pantothenate-containing product prepared in this way had a pantothenic acid concentration of 68.5 wt. % was free-flowing and had a bulk density of 460 mg/ml. After being stored for five months, the concentration of D-pantothenic acid was 67.6 wt. %.

Example 4

Preparing Sodium D-Pantothenate

The biomass was first separated from a pantothenic acid-containing fermentation broth which had been prepared using the process described in Examples 1 and 2 and which contained about 6.1 wt. % of D-pantothenic acid. For this, 1 l of the fermentation broth mentioned above was centrifuged and ultrafiltered in the same way as described in Example 3.

Then 10.6 g of NaOH (99%; Merck) were added batchwise, with stirring. The pH was then about 10. The broth treated in this way was then concentrated under vacuum at 50–60° C. in a rotary evaporator, a Rotavapor RE-120 from Büchi-Labortechnik GmbH, to a liquid concentration of about 50% dry weight. The broth concentrated in this way was then freeze-dried in a freeze-dryer, a LYOVAC GT 2 from Leybold (Cologne, Germany), to prepare the sodium salt of D-pantothenic acid.

The sodium D-pantothenate-containing product prepared in this way had a D-pantothenic acid concentration of 63.8 wt. % and was free-flowing. After being stored for five months, the concentration of D-pantothenic acid was 63.0 wt. %.

Example 5

Preparing Magnesium D-Pantothenate

The biomass was first separated from a pantothenic acid-containing fermentation broth which had been prepared using the process described in Examples 1 and 2 and which contained about 6.1 wt. % of D-pantothenic acid. For this, 1 l of the fermentation broth mentioned above was centrifuged and ultrafiltered in the same way as described in Example 2.

Then 5.4 g of solid MgO (97%; Merck) were added batchwise, with stirring. The pH was then about 9 to 10. The broth treated in this way was then concentrated under vacuum at 50–60° C. in a rotary evaporator, a Rotavapor RE-120 from Büchi-Labortechnik GmbH, to a liquid concentration of about 50% dry weight. The broth concentrated in this way was then freeze-dried in a freeze-dryer, a LYOVAC GT 2 from Leybold to prepare the magnesium salt of D-pantothenic acid.

The magnesium D-pantothenate-containing product prepared in this way had a D-pantothenic acid concentration of 64.7 wt. % and was free-flowing. After being stored for five months, the concentration of D-pantothenic acid was 64.4 wt. %.

Example 6

Preparing Potassium D-Pantothenate

The biomass was first separated from a pantothenic acid-containing fermentation broth which had been prepared using the process described in Examples 1 and 2 and which contained about 6.1 wt. % of D-pantothenic acid. For this, 1 l of the fermentation broth mentioned above was centrifuged and ultrafiltered in the same way as described in Example 2.

Then 17.4 g of KOH (85%; Merck) were added batchwise, with stirring. The pH was then about 10 to 11. The broth treated in this way was then concentrated under vacuum at 60° C. in a rotary evaporator, a Rotavapor RE-120 from Büchi-Labortechnik GmbH, to a liquid concentration of about 50% dry weight. The broth concentrated in this way was then freeze-dried in a freeze-dryer, a LYOVAC GT 2 from Leybold, to prepare the potassium salt of D-pantothenic acid.

The potassium D-pantothenate-containing product prepared in this way had a D-pantothenic acid concentration of 63.5 wt. % and was free-flowing. After being stored for five months, the concentration of D-pantothenic acid was 62.9 wt. %.

Example 7

Preparing Ammonium D-Pantothenate

The biomass was first separated from a pantothenic acid-containing fermentation broth which had been prepared using the process described in examples 1 and 2 and which contained about 6.1 wt. % of D-pantothenic acid. For this, 1 l of the fermentation broth mentioned above was centrifuged and ultrafiltered in the same way as described in Example 2.

The broth treated in this way was then concentrated under vacuum at 60° C. in a rotary evaporator, a Rotavapor RE-120 from Büchi-Labortechnik GmbH, to a liquid concentration of about 50% dry weight. The broth concentrated in this way was then freeze-dried in a freeze-dryer, a LYOVAC GT 2 from Leybold, to prepare the ammonium salt of D-pantothenic acid.

The ammonium D-pantothenate-containing product prepared in this way had a D-pantothenic acid concentration of 66.8 wt. % and was free-flowing.

Example 8

Preparing Calcium D-Pantothenate from a Biomass-containing Fermentation Broth A pantothenic acid-containing fermentation broth which had been prepared using the method described in Examples 1 and 2 and which contained about 6.1 wt. % of D-pantothenic acid was first concentrated under vacuum at 60° C. in a rotary evaporator, a Rotavapor RE-120 from Büchi-Labortechnik GmbH (Konstanz, Germany) a volume of 1.0 l to a liquid concentration of about 30% dry weight. Then 10.1 g of solid Ca(OH)$_2$ (96%; Merck, Darmstadt, Germany) were added batchwise, with stirring. The pH was then about 10. The biomass-containing broth treated and concentrated in this way was then spray dried to prepare the calcium salt of D-pantothenic acid. For this, a laboratory spray dryer, a Büchi-190 from Büchi-Labortechnik GmbH (Konstanz, Germany), was used with an inlet temperature of 107° C., an outlet temperature of 85° C., a pressure difference of −40 mbar and a rate of flow of air of 600 NL/h.

The calcium D-pantothenate-containing product prepared in this way had a concentration of D-pantothenic acid of 49.8 wt. %, was free-flowing and had a bulk density of 480 mg/ml. The biomass content was about 30 wt. %.

Example 9

Preparing a Product which Contains a Calcium D-Pantothenate and Biomass from *Corynebacterium Glutamicum*

1. Preparing a Pantothenic Acid-producing Strain of *Corynebacterium Glutamicum*

U.S. Pat. No. 5,188,948 describes the L-valine producing strain *Brevibacterium lactofermentum* FERM BP-1763. DE 19855313.7 discloses the plasmid pND-DBC2 (FIG. 1), which contains the genes panB, panC and panD from *Corynebacterium glutamicum*. The plasmid is deposited as DSM 12437 at the Deutschen Sammiung für Mikroorganismen und Zelikulturen (German collection of microorganisms and cell cultures) (Braunschweig, Germany), in the form of the strain ATCC13032/pND-DBC2. The pantothenic acid-producing strain FERM BP-1763/pND-DBC2 is obtained by transforming the strain FERM BP-1763 with the plasmid pND-DBC2.

2. Preparing a Pantothenic Acid-containing Fermentation Broth

A sample of *Brevibacterium lactofermentum* FERM BP-1763/pND-DBC2 was painted onto HHK agar.

HHK agar is a brain/heart agar, which is sold by Merck KgaA (Darmstadt, Germany) and was supplemented with kanamycin. The composition of the HHK agar is given in Table 1a.

This agar plate culture was incubated at 37° C. for 17 hours and then stored in a refrigerator at +4° C. Individual selected colonies were then propagated further on the same medium. Cell material from a clone was then taken from the HHK agar and transferred, using an inoculation ring, into 100 ml of HHK broth, which had been placed in a shaker flask with a total volume of 1000 ml.

HHK broth is a brain/heart medium that is sold by Merck KgaA (Darmstadt, Germany) and had been supplemented with glucose and kanamycin. The composition of HHK broth is given in Table 1b.

TABLE 1a

| HHK agar | |
|---|---|
| Substance | Amount per liter |
| Brain/heart agar | 52.0 g |
| Kanamycin | 25 mg |

TABLE 1b

| HHK broth | |
|---|---|
| Substance | Amount per liter |
| Brain/heart medium | 37.0 g |
| Kanamycin | 25 mg |
| Glucose | 20.0 g |

The mixture was incubated for 22 hours at 30° C. and 150 rpm. After completion of the cultivation process, an optical density of 6.1 was measured in a photometer at a wavelength of 660 nm (OD 660). This culture of the strain FERM BP-1763/pND-DBC2 was used to inoculate the production fermenter.

The medium SK-71 given in Table 1c was used for fermentation. All the components in the SK-71 medium were initially introduced directly into the fermenter in accordance with the working concentrations and sterilized in situ.

TABLE 1c

| Medium SK-71 | |
|---|---|
| Compound | Amount per liter |
| Glucose hydrate | 110.0000 g |
| Cornsteep liquor (CSL) | 5.0000 g |
| β-alanine | 5.0000 g |
| Nicotinic acid | 0.0050 g |
| I-isoleucine | 0.1500 g |
| Homoserine | 0.1500 g |
| Ammonium sulfate | 25.0000 g |
| K dihydrogen phosphate | 0.1000 g |
| Mg sulfate 7H$_2$O | 1.0000 g |
| Fe sulfate 7H$_2$O | 0.0100 g |
| Mn sulfate H$_2$O | 0.0050 g |
| CaCl$_2$ * 2H$_2$O | 0.0100 g |
| Thiamine HCl | 0.0002 g |
| D(+)biotin | 0.0003 g |
| Struktol | 0.60 g |

10 l stirred reactors from the B. Braun Co. (BBI, Germany, Melsungen, Model Biostat E/ED) were used as fermenters.

100 ml of the shaker flask preculture in HHK broth described above were used to inoculate 1950 g of fermentation medium SK-71.

The mixture was cultivated over the entire fermentation time at a temperature of 30° C., a volume-specific rate of aeration of 0.75 vvm, a rate of stirring of 800–1700 rpm, which depended on the consumption of oxygen and a pH of 7.0 and an oxygen partial pressure of 20% of air saturation. The culture was cultivated in total for 49 hours under the conditions given above until an OD660 of 26.2 was achieved. An aqueous ammonia solution (25% w/v) was used as the correction medium to regulate the pH.

Then the optical density (OD) was determined using a digital photometer of the LP1W type from the Dr. Bruno Lange GmbH Co. (Berlin, Germany) at a measurement wavelength of 660 nm and the concentration of D-pantothenic acid was determined using HPLC (Hypersil APS 2 5 μm, 250×5 mm Rl detection).

A D-pantothenic acid concentration of about 0.2 g/l was measured in the final fermentation sample after 49 hours.

3. Preparing a Pantothenic Acid-containing Product

A D-pantothenic acid-containing fermentation broth with a concentration of about 0.02 wt. % of D-pantothenic acid was prepared using the method in Example 9.2. A volume of 1.4 l of this fermentation broth was first evaporated down to a broth with a dry solids content of about 15% under vacuum at 60° C. in a rotary evaporator of the Rotavapor RE-120 type made by Büchi-Labortechnik GmbH (Konstanz, Germany). Then 27.1 g of solid Ca(OH)$_2$ (96%; Merck, Darmstadt, Germany) were added in portions with stirring. The pH was then about 10.0. 37.7 g of calcium D-pantothenate ($\geq$98%, Euro OTC Pharma GmbH, Kamen, Germany) were then added to the biomass-containing broth treated and concentrated in this way. A laboratory spray dryer of the Büchi-190 type from Büchi-Labortechnik GmbH (Konstanz, Germany) was used for the final spray drying procedure at an input temperature of 107° C., a discharge temperature of 85° C., a pressure difference of –40 mbar and a rate of flow of air of 600 Nl/h.

The calcium D-pantothenate-containing product prepared in this way had a D-pantothenic acid concentration of about 35%, was pourable and had a bulk density of 600 mg/ml. The proportion of *C. glutamicum*—biomass was about 3.5 wt. %.

Example 10

Preparing a Product Containing Calcium D-Pantothenate and Biomass from *Saccharomyces Cerevisiae*

1. Preparing a Pantothenic Acid Producing Strain of *Saccharomyces Cerevisiae*

Amplification of the reading frame YHR063c:
Starting with the nucleotide sequence for *Saccharomyces cerevisiae* reading frame YHR063c (Accession No. U00061 at the National Center for Biotechnology, Bethesda, Md, USA), the following PCR primers were synthesized (MWG-Biotech, Ebersberg, Germany). The start and end of the reading frame are represented by a period (.):

oJD539 (5' EcoRl-Notl START):
5'-GCG CGA ATT CAG ATC CGC GGC CGC AAA GAG GAG AAA TTA ACT ATG ACT GCA CCA CAC AGA AG-3'(SEQ ID NO.:1)

oJD540 (3' Spel-Pstl STOP):
5'-CGC GAC TAG TCT GCA GTC AGT CCT TTC TCC AGT CAC-3'(SEQ ID NO.:2)

Genomic DNA from *S. cerevisiae* strain JD242 which had been isolated using the C. Guthrie and G.R. Fink method (Guide to yeast genetics and molecular biology, Methods in Enzymology, Vol. 194, Academic Press, San Diego, Calif., 1991) was used as template. This strain is a haploid segregant of the diploid strain SC288C (Winston et al., Yeast 11, 53ff. (1995)), whose genome has been sequenced (Goffeau et al., Science 274, pp. 546, (1996)). Tetrad analysis was performed by the C. Guthrie und G. R. Fink method (Guide to yeast genetics and molecular biology, Methods in Enzymology, Vol. 194, Academic Press, San Diego, Calif., 1991). The strain JD242 is auxotrophic for leucine (leu2$\Delta$1 allele) and uracil (ura3-52 allele). An approximately 1.2 kB sized DNA fragment was amplified by 28 PCR cycles under the conditions cited by the manufacturer, using "High Fidelity Expand Polymerase" kits from the Roche Co. (Mannheim). The size was determined by electrophoretic separation in a 0.8% strength agarose gel.

Structure of pJD-YHR063c:
In order to express YHR063c reading frame in *S. cerevisiae* the PCR amplificate was incorporated into *E. coli—S. cerevisiae* shuttle vector pJDCEX2 (FIG. 2 and Dohmen et al., 1995, Journal of Biological Chemistry 270, 18099–18109).

The PCR product was first restrung with EcoRl and Spel (AGS, Heidelberg, Germany). Then it was mixed with pJDCEX2-DNA, which had been treated with EcoRl and Xbal (AGS, Heidelberg, Germany) and ligated with T4-DNA ligase (Roche, Mannheim, Germany). The ligation mixture was transformed in *E. coli* strain XL1-blue (Bullock et al., 1987, Biotechniques 5,376). The transformants were obtained by selection on LB agar, which contained 150 μg/ml ampicillin (Sigma, Deisenhofen, Germany). The plasmid DNA from the ampicillin-resistant clones was prepared by alkaline cell lysis (Sambrook et al.: Molecular Cloning, A Laboratory Manual, Cold Spring Harbor Laboratory Press, 1989). The isolated plasmid DNA was then tested by restriction using Notl and Pstl and subsequent separation in 0.8% strength agarose gel. The plasmid with the desired structure was given the name pJD-YHR063c (FIG. 3).

Preparing strain JD242/pJD-YHR063c:
*S. cerevisiae* strain JD242 was transformed with the plasmid pJD-YHR063c using Dohmen et al.'s method (Dohmen et al., Yeast 7, 691 (1991)). Selection of transformants was performed on leucine-free minimal medium SD using 1.8% agar, as set forth in Tables 2a and 2b.

TABLE 2a

Minimal medium SD

| Compound | Amount per liter |
|---|---|
| (NH$_4$)$_2$ SO$_2$ | 5 g |
| KH$_2$PO$_4$ | 1 g |
| MgSO$_4$ * 7 H$_2$O | 0.5 g |
| NaCl | 0.1 g |
| CaCl$_2$ | 0.1 g |
| H$_3$BO$_3$ | 500 μg |
| CuSO$_4$ | 40 μg |
| KI | 100 μg |
| FeCl$_3$ * 6 H$_2$O | 200 μg |
| MnSO$_4$ * H$_2$O | 400 μg |
| Na$_2$MoO$_4$ * 2 H$_2$O | 400 μg |
| ZnSO$_4$ * 7 H$_2$O | 200 μg |
| Biotin | 2 μg |
| Folic acid | 2 μg |
| Inositol | 2 mg |
| Niacin | 400 μg |
| p-aminobenzoic acid | 200 μg |
| Pyridoxine hydrochloride | 400 μg |
| Riboflavine | 200 μg |
| Thiamine hydrochloride | 400 μg |

TABLE 2b

Minimal medium SD

| Added substances | Amount per liter |
|---|---|
| Glucose | 20 g |
| Uracil | 40 mg |
| CuSO$_4$ | 24 mg |
| –Leu DO supplement | 650 mg |
| Ketopantoate | 100 mg |
| β-alanine | 100 mg |

2. Preparing a Pantothenic Acid-containing Fermentation Broth

To prepare a D-pantothenate-containing fermentation broth, an individual colony of *S. cerevisiae* strain JD242/pJD-YHR063c was first painted onto an agar plate with minimal medium SD and incubated for 3 days at 30° C. To prepare this first preculture in shaker flasks, the cells were then floated off with ml of minimal medium SD. Each shaker flask (500 ml total volume) containing 50 ml of minimal medium SD (Tables 2a and 2b) was then inoculated with 2.5 ml of this cell suspension and cultivated for 6 hours at 30° C. and 130 rpm on a RC-1-TK incubator from Infors AG (Bottmingen, Switzerland), until an optical density of 1.9 could be measured at a wavelength of 660 nm (OD660). The second preculture was made up in a 1000 ml baffle-flask in 150 ml of minimal medium SD (Tables 2a and 2b) and each of these was inoculated with 50 ml of preculture 1 described above. Incubation was performed for 20 hours at 30° C. and 80 rpm until an optical density of about 3.8 was achieved at a wavelength of 660 nm (OD 660). The main fermentation in order to produce pantothenic acid was performed in round-bottomed flasks with a 6000 ml total volume, in 1500 ml of minimal medium SD (Tables 2a and 2b). For this purpose, the round-bottomed flasks were each inoculated with 90 ml of preculture 2 and then incubated for 30 hours at 30° C. and 60 rpm.

The optical density (OD) was measured with a digital photometer of the LP1W type from Dr. Bruno Lange GmbH (Berlin, Germany) at a measurement wavelength of 660 nm. The concentration of D-pantothenic acid obtained was determined using the strain *Lactobacillus plantarum* ATCC® 8014 in accordance with data in the manual "DIFCO MANUAL" from DIFCO (Michigan, USA;, 10$^{th}$ Edition, 1100–1102 (1984).

The optical density (OD660) was about 4 and the concentration of D-pantothenic acid was about 1 mg/l.

3. Preparing a Pantothenic Acid-containing Product

A pantothenic acid-containing fermentation broth with a concentration of about 1 mg/l of D-pantothenic acid was prepared using the method in Example 10.2. A volume of 6.0 l was first evaporated down to give a broth with about a 16% dry solids content, under vacuum at 60° C. in a rotary evaporator of the Rotavapor RE-151 type from Büchi-Labortechnik GmbH (Konstanz, Germany). Then 15.9 g of solid $Ca(OH)_2$ (96%; Merck, Darmstadt, Germany) were added in portions with stirring. The pH was then about 9.2. 28.4 g of calcium D-pantothenate(>98%, Euro OTC Pharma GmbH, Kamen, Germany) were then added to the biomass-containing broth treated and evaporated down in this way. The broth was then freeze-dried in a freeze-dryer of the LYOVAC GT 2 type from the Leybold Co. (Cologne, Germany).

The calcium D-pantothenate-containing product prepared in this way had a D-pantothenic acid concentration of 26.5 wt. %, was pourable and had a bulk density of 450 mg/ml. The proportion of *S. cerevisiae* biomass was about 6.8 wt. %.

What is claimed is:

1. Animal feedstuff additives comprising:
   a) at least one member of the group consisting of D-pantothenic acid and D-pantothenic acid salts;
   b) 0 to 100% of a biomass formed during fermentation in a fermentation broth of microorganisms which produce D-pantothenic acid, the microorganisms being selected from the group consisting of Corynebacterium glutamicum, Brevibacterium lactofermentum and Saccharomyces cerevisiae; and
   c) dissolved ingredients in the fermentation broth,
wherein said feedstuff additives are present in a solid, finely divided or granulated, free-flowing form.

2. The animal feedstuff additives according to claim 1, wherein the D-pantothenic acid salts are selected from the group consisting of sodium, potassium, ammonium, magnesium and calcium salts of D-pantothenic acid.

3. The animal feedstuff additives according to claim 1, wherein the at least one D-pantothenic acid or D-pantothenic acid salts are present in an amount between 20 to 80 wt. %, (dry weight).

4. The animal feedstuff additives according to claim 1, wherein the additives are formulated as a spray dried powder.

5. The animal feedstuff additives according to claim 1, further comprising one or more L-amino acids selected from the group consisting of L-methionine, L-lysine, L-valine, L-alanine, L-threonine and L-tryptophane.

6. A process for preparing feedstuff additives containing at least one member of the group consisting of D-pantothenic acid and D-pantothenic acid salts comprising a) obtaining a D-pantothenic acid-containing fermentation broth formed during fermentation of microorganisms selected from the group consisting of Corynebacterium glutamicum, Brevibacterium lactofermentum and Saccharomyces cerevisiae;

b) optionally, at least partially removing a fermentation biomass, from the fermentation broth;

c) adding a hydroxide or oxide of an alkaline earth or alkali metal to the broth of step b) to form a solution; and d) drying the solution of step c).

7. A process according to claim 6, wherein drying is achieved by spray-drying.

8. A process according to claim 6, wherein the oxide or hydroxide, is a member selected from the group consisting of sodium, potassium, ammonium, magnesium or calcium compounds.

9. A process according to claim 6, wherein the oxide or hydroxide is added in a stoichiometric ratio of 0.8 to 1.2 with respect to the D-pantothenic acid.

10. A process according to claim 9, wherein the oxide or hydroxide is added in a stoichiometric ratio of 0.95 to 1.1 with respect to the D-pantothenic acid.

11. A process for preparing feedstuff additives containing at least one member selected from the group consisting of D-pantothenic acid a sodium salt of D-pantothenic acid, a potassium salt of D-pantothenic acid, an ammonium salt of D-pantothenic acid, a magnesium salt of D-pantothenic acid and a calcium salt of D-pantothenic acid comprising a) obtaining a D-pantothenic acid-containing broth from fermentation of a microorganism;

b) optionally, at least partially removing a fermentation biomass from the fermentation broth;

c) optionally, concentrating the fermentation broth of step b); and d) drying to obtain the feedstuff additive.

12. A process according to claim 11, wherein drying is accomplished by spray drying.

13. A process according to claim 11, further comprising adding an oxide or hydroxide of alkali metals or alkaline earth metals to the fermentation broth before or after concentrating.

14. A process according to claim 13, wherein the microorgansims are selected from the group consisting of fungi, bacteria from the genus Coryenbacterium,and bacteria from thee family Enterobacteriaceae.

15. A process according to claim 11, further comprising adding one or more L-amino acids, selected from the group consisting of L-lysine, L-valine, L-alanine, L-threonine and L-tryptophan, to the optionally concentrated fermentation broth.

* * * * *